United States Patent

Sgro

[11] Patent Number: 5,840,055
[45] Date of Patent: Nov. 24, 1998

[54] DISPOSABLE DEVICE FOR TRANSFER OF AN ACTIVE LIQUID INTO AN INTRACORPOREAL CAVITY

[75] Inventor: Jean-Claude Sgro, Dijon, France

[73] Assignee: Bernard Chaffringeon, Saint-Sulpice, Switzerland

[21] Appl. No.: 817,945
[22] PCT Filed: Nov. 17, 1995
[86] PCT No.: PCT/FR95/01521
§ 371 Date: Jul. 15, 1997
§ 102(e) Date: Jul. 15, 1997
[87] PCT Pub. No.: WO96/15724
PCT Pub. Date: May 30, 1996

[30] Foreign Application Priority Data

Nov. 21, 1994 [FR] France ................................ 94 14249

[51] Int. Cl.⁶ .............................. A61F 13/20; A61F 5/44; A61M 1/00
[52] U.S. Cl. .............................. 604/11; 604/904; 604/54; 604/93; 604/28; 604/328; 604/330; 604/331; 600/309; 600/573; 600/582; 600/584
[58] Field of Search ............................... 604/11–18, 904, 604/285–288, 54, 56, 82, 93, 28, 328–331, 89.1; 600/309, 342, 573, 582, 584

[56] References Cited

U.S. PATENT DOCUMENTS

| | | |
|---|---|---|
| 2,493,416 | 1/1950 | Negri ....................................... 604/904 |
| 3,519,364 | 7/1970 | Truhan et al. . |
| 4,232,673 | 11/1980 | Bucalo ..................................... 128/769 |
| 4,257,427 | 3/1981 | Bucalo . |
| 4,286,596 | 9/1981 | Rubinstein .............................. 604/904 |
| 4,317,454 | 3/1982 | Bucalo . |
| 5,273,521 | 12/1993 | Peiler et al. .............................. 604/13 |
| 5,299,581 | 4/1994 | Donnell et al. ......................... 604/286 |
| 5,357,977 | 10/1994 | Michels . |

FOREIGN PATENT DOCUMENTS

| | | |
|---|---|---|
| 2353640 | 12/1977 | France . |
| 80/01353 | 7/1980 | WIPO . |
| 83/01741 | 5/1983 | WIPO . |

Primary Examiner—John G. Weiss
Assistant Examiner—Dennis Ruhl
Attorney, Agent, or Firm—Oliff & Berridge, PLC

[57] ABSTRACT

A disposable device for transfer of an active liquid into an intracorporeal cavity, having a central element able to contact the mucous membrane of an intracorporeal cavity; an absorbent peripheral element arranged around the central element that absorbs liquid; a temporary protective covering, that is sealed with respect to liquids, that prevents fluid communication between the peripheral element and the central element; an active liquid contained in the central element or the peripheral element; and a means for recovering the active liquid, which has circulated in the intracorporeal cavity, that is contained in the peripheral element or the central element, respectively.

22 Claims, 5 Drawing Sheets

DISPOSABLE DEVICE FOR TRANSFER OF AN ACTIVE LIQUID INTO AN INTRACORPOREAL CAVITY

BACKGROUND OF THE INVENTION

The present invention relates to the transfer or circulation of an active liquid into or inside an intracorporeal cavity of the human body or of an animal, in particular in contact with the mucous membrane of said cavity.

Intracorporeal cavity is understood as meaning any cavity of the body, in particular an elongate cavity, to which it is possible to gain access from the outside for different purposes, in particular for clinical, therapeutic, prophylactic or diagnostic purposes, but also for cosmetic purposes or for purposes of personal hygiene. An example which may be mentioned of one such cavity is the vagina, which extends from the vulva to the neck of the uterus and into which/in which it is desired to transfer/circulate an active liquid mixing with the cervical mucus, for example.

Consequently, the active liquids taken into consideration in the present invention are generally treatment liquids or fluids, including both a liquid agent for wetting, solubilizing or fluidizing, in particular of a body liquid or fluid present in the intracorporeal cavity in question, and also a therapeutic, prophylactic or diagnostic agent, or even a cosmetic agent or an agent for personal hygiene, or finally an antiseptic, bactericidal, fungicidal or spermicidal agent in the case of the vaginal cavity for example.

SUMMARY OF THE INVENTION

The subject of the present invention is a disposable device, such as has been defined above, ensuring an almost total absence of external flow, either of the active liquid and/or of the body fluids or liquids, or of any fluid present in the intracorporeal cavity in question, throughout the entire time that said device is present or held in said cavity; to this end, according to the invention, the device comprises:

- a central element having means for contact or exchange with the mucous membrane or the inside of the intracorporeal cavity in question;
- a peripheral element arranged around the central element, in particular concentric to the latter, comprising a tampon designed to absorb all liquid or fluid by expanding, and by virtue of this coming to bear sealingly against the mucous membrane or wall of said intracorporeal cavity;
- a temporary means of protection, sealed with respect to the liquids or fluids present in said cavity, for protecting the peripheral element in relation to the central element, or vice versa; the central element and the peripheral element are arranged or designed to communicate with one another in the intracorporeal cavity, once the temporary means of protection has been withdrawn;
- a source of active liquid, contained in the central element or the peripheral element;
- and a means for recovering the active liquid, which has circulated in the intracorporeal cavity, said means being contained in the peripheral element or the central element, respectively.

This disposable device can be completed with an element for application to the inside of the intracorporeal cavity, mounted on the central element and/or the peripheral element in such a way that it is integral in the direction of introduction into said cavity, and in such a way that it is detachable in the opposite direction.

For the purposes of removing a sample and/or for performing an analysis of the body fluid or liquid present in the intracorporeal cavity in question, the device can additionally comprise:

- an element for transporting of the active liquid which has circulated in the intracorporeal cavity, and optionally mixed with said body fluid or liquid, said element being in an elongate shape, for example a small cord, in flow continuity at one end with the central element or the peripheral element, respectively;
- an outer element for extemporaneous analysis of a constituent of the body fluid or liquid, mixed with the active liquid, or of a biochemical, chemical, or biological state of said body fluid; this analysis element is arranged at the free end of the transport element.

"Constituent" of the body fluid or liquid is understood as meaning not only a chemical or biochemical constituent, but also a biological or living constituent, for example a cellular constituent.

By way of example, taking the cervical mucus into consideration as a body fluid, and for the purposes of detecting the periods of fertility in women, the biochemical or biological constituent to be analyzed is a peroxidase or a compound having a peroxidase activity, and the outer element for extemporaneous analysis comprises or forms a reagent or a system of reagents, in particular colored, for example an oxidation-reduction compound, of which at least the oxidized form is colored, for example guaiacol.

"Analysis" is understood as meaning any method or device by which it is possible to identify, separate, enrich or quantify the constituent or analyte being tested for in the body fluid, or any state of the latter, for example its acidity or pH.

BRIEF DESCRIPTION OF THE DRAWINGS

The present invention is now described with reference to the attached drawing, in which.

DESCRIPTION OF THE PREFERRED EMBODIMENT

Figure 2:
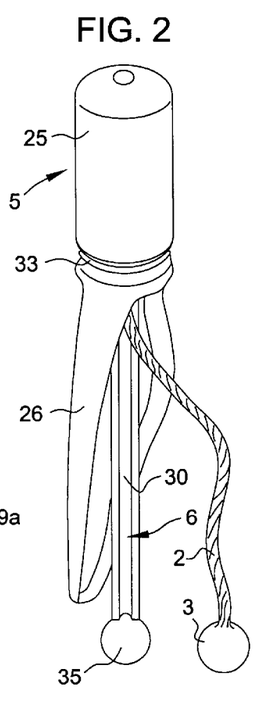
FIG. 2 represents a perspective view of the device represented inn FIG. 1, ready for use.
Figure 3:
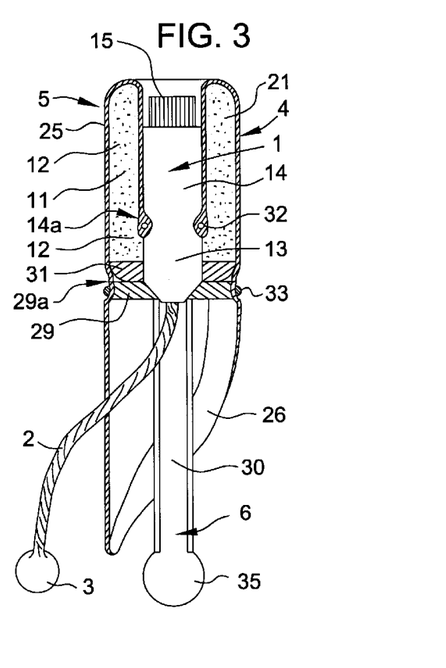
FIG. 3 represents an axial cross section of the device represented in FIGS. 1 and 2.
Figures 4, 5:
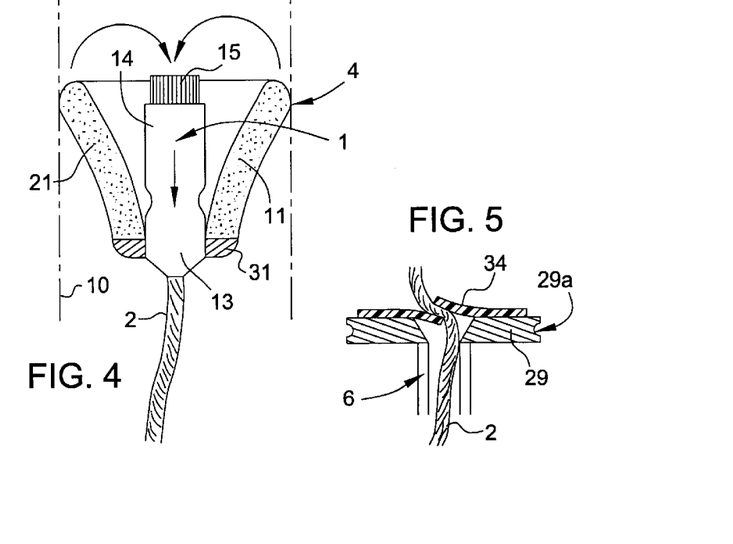
FIG. 4 represents a cross section of the central and peripheral elements of the device represented in FIGS. 1 to 3, once introduced and held in an intracorporeal cavity, after the temporary means of protection of the peripheral element has been removed.
FIG. 5 represents a cross section of a detail of the device represented in FIGS. 1 to 3.

In accordance with FIGS. 1 to 5, a disposable device according to the invention for transfer of an active liquid into an intracorporeal cavity, which is represented in a diagrammatic manner in FIG. 4 by reference number 10, has a general shape and possesses an inherent stiffness which is sufficient to permit its introduction by pushing, and to hold it in place in the cavity 10 by simple constriction of the latter.

In a general manner, this device comprises:
- a central element 1 having means for contact or communication with the mucous membrane or the inside of the intracorporeal cavity 10;
- a peripheral element 4 arranged around, and more precisely concentrically around, the central element; this element comprises a tampon 11 designed or chosen to absorb all liquid or fluid by expanding, and by virtue of this coming to bear sealingly against the mucous membrane of the intracorporeal cavity 10;
- a temporary means 5 of protection, sealed with respect to the liquids, for protecting the peripheral element 4 in relation to the central element 1; the central element 1 and the peripheral element 4 are arranged, as shown in FIG. 4, to communicate with one another in the intracorporeal cavity 10, once the temporary means 5 of protection has been withdrawn;
- a source 12 of active liquid, contained in the peripheral element 4;
- a means for recovering 13, in a first embodiment the active liquid, which has circulated in the intracorporeal cavity, and which may optionally have carried with it a body fluid or liquid, this means being contained in the central element 1;
- an element for application 6 to the inside of the intracorporeal cavity 10, mounted on the central element 1 and/or the peripheral element 4, in such a way that it is integral in the direction of introduction into said cavity 10, and in such a way that it is detachable in the opposite direction;
- a transport element 2, for example a wick, for transporting the active liquid which has circulated in the intracorporeal cavity 10, and being of elongate shape, for example a small cord, in continuity at one end with the central element 1, and more precisely the recovery means 13 in a first embodiment;
- and an outer element 3 for extemporaneous analysis of a constituent of the body fluid present in the intracorporeal cavity 10, mixed with the active liquid, or for extemporaneous analysis of a biochemical, chemical or biological state of this same body fluid; this analysis element is arranged at the free end of the transport element 2.

Figure 1:
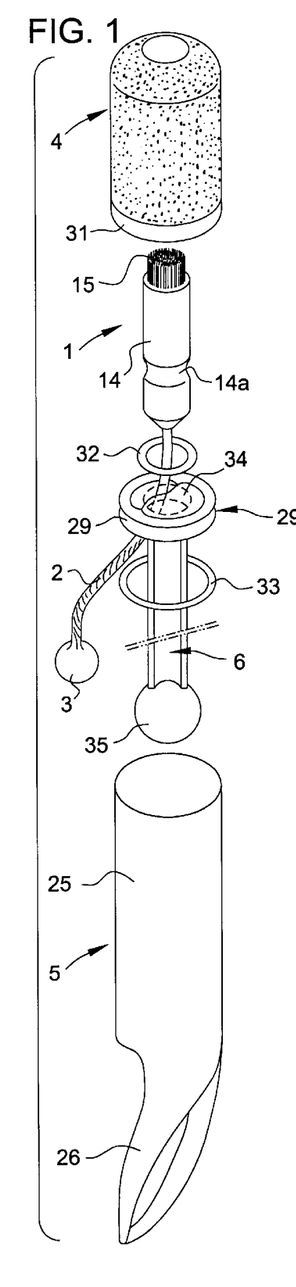
FIG. 1 represents an exploded view of a device according to a first embodiment of the invention.

The central element 1 comprises a core 14 provided with filiform means 15, in particular capillary filaments, for contact with the mucous membrane of the intracorporeal cavity. These filiform means are held in shape by the temporary means of protection 5 described hereinafter.

The capillary filaments 15 can be made from any synthetic or natural material, in particular biocompatible material, for example natural absorbent fibers (cotton, flax, etc.).

The peripheral element 4 comprises a sleeve 21 made of a material which is capable of absorbing a liquid or fluid by expanding, and surrounding the core 14 of the central element 1, provided with filiform elements 15.

The absorbent material of the sleeve 21 is expandable and/or spongy and consists, for example, of filaments, capillary fibers, or natural fibers, etc.

This sleeve has a cylindrical shape when it is held by the temporary means 5 of protection described hereinafter, and evolves toward a corolla shape once the temporary protection means 5 has been removed, and the device according to the invention introduced and held blocked in the intracorporeal cavity (cf. FIG. 4).

The absorbent material of the sleeve 21 is impregnated until saturation with the active liquid, for example a physiological saline, and/or a nonagressive fluidizing agent, and/or a therapeutic agent with local diffusion. It is maintained in a nonexpanded configuration by the temporary means of protection 5 described hereinafter. It is in the cylindrical central orifice of the sleeve 21 that the central element 1 described above is arranged. The lower part 31 of the sleeve 21 is impermeable, either by impregnation of the absorbent material with a suitable product, or by adding an impermeable sheet.

The temporary means 5 of protection comprises a sheath 25 surrounding or enclosing at least partially, in a sealing manner, the peripheral element 4 all around the central element 1. This sheath has or is integral with an end of an attachment 26, for example a pull loop, by which it is possible to withdraw the sheath 25 in order to expose the peripheral element 4 in the intracorporeal cavity 10.

With the exception of the loop part or attachment 26, this sheath 25 has the general shape of a sock partially turned back on itself and around the sleeve 21. The inner free edge of the sheath 25 is held in sealing contact in a circular groove 14a of the core 14, by means of an O-ring seal 32, or an easily tearable weld seam. In the same way, the annular transition zone between the sock part and the loop part 26 of the sheath 25 is held tight, in sealing contact, in a groove 29a of the bearing element 29, described hereinafter, of the application element 6, by means of an O-ring seal 33, or by an easily tearable weld seam, but one which is sufficiently strong to maintain the sealing inside the sock part of the sheath 25. If appropriate, the sheath 25 can be held sufficiently tight on the peripheral element 4, or more precisely on the impermeable base 31 of the sleeve 21, again in a sealing manner.

The sheath 25 is made of an impermeable material, in particular a biocompatible material, for example a heat-shrinkable plastic. It is very fine, but is sufficiently strong to make it possible, by pulling on the loop 26, as described hereinafter, to break the sealing connections at the level of the grooves 14a, 29a, and if appropriate the base 31, then to unroll the sock-shaped envelope part, and to separate it or withdraw it from the device, releasing the peripheral element 4, and exposing it within the intracorporeal cavity 10.

Furthermore, the sheath 25, of general cylindrical shape, is sufficiently flexible and fine, as well as smooth and slidable on its outer face, to facilitate the introduction of the device into the intracorporeal cavity.

The transport element 2 serves at the same time to direct the active liquid, and if appropriate the body fluid or fluids removed by means of the latter, as far as the analysis element 3. It also serves to withdraw the whole device according to the invention following use. The transport element 2 has a diameter which is sufficiently fine to ensure that it does not cause any inconvenience or discomfort in the body cavity. This element can be single or twin and can be in the form of a coarse string or a small cord, for example.

The analysis element 3 is in flow continuity with the transport element 2. This element 3 supports suitable reagents, deposited for this purpose. This analysis element 3 advantageously has a spherical shape. However, in the case where this element does not form a small sphere or a cylinder, the reagents are deposited at the free end of the small cord or at the external part of a twin cord.

The application element 6 comprises a bearing element 29, for example a disk, fixed to the end of an axial rod 30, for example a diametrally recessed tube. The central element 1 is mounted in a sealed manner at one end, against and within an adapted orifice of the disk 29, both being aligned with the axial rod 30. As is shown more particularly in FIG. 5, the sealed passage of the transport element 6 in the orifice formed on the disk 29 is ensured by means of an elastic seal 34. The axial rod 30, having the form of a slotted tube, is adapted for the passage of the transport element 2. The axial rod 30 terminates in a bulged portion 35 in order to facilitate the handling and the withdrawal of the application element 6.

The device described above is used or implemented in the following manner, starting with the configuration represented in FIG. 2:

- by pushing on the application element 6, the device is introduced into the intracorporeal cavity 10, which holds it in position by simple constriction;
- by pulling on the loop 26, the sheath 25, or temporary means of protection 5, is released from the central element 1 and the peripheral element 4, the sheath 25 is unrolled or unfolded, and it is withdrawn from the intracorporeal cavity by sliding along the peripheral element 4;
- the peripheral element 4 is released and thus expands, in relatively sealing contact with the intracorporeal cavity 10, as is shown in FIG. 4, which fact also ensures that it is held in place;
- from this moment, the active liquid is released into the cavity 10 and carries with it the body fluid which is present in the cavity 10, both moving toward the central element 1 by way of the filiform means 15 and the recovery means 13 in a first embodiment, all toward the analysis element 3, which can be observed or visualized by the user, outside the cavity 10;
- once the reaction or absence of reaction has been demonstrated, it is possible, by pulling on the transport element 2, to withdraw the device and then dispose of it.

The device described above additionally affords the following important advantages:

- its use is particularly simple, reliable and effective;
- since the chemical and/or biological products necessary for the analysis are outside the intracorporeal cavity, there can be no irritation, or even burning, in contact with the living tissue, and more particularly at the level of the mucous membranes of the intracorporeal cavity;
- the analysis results can be read off directly without any manipulation of, or direct contact with, the chemical or biological reaction products.

Figure 6:
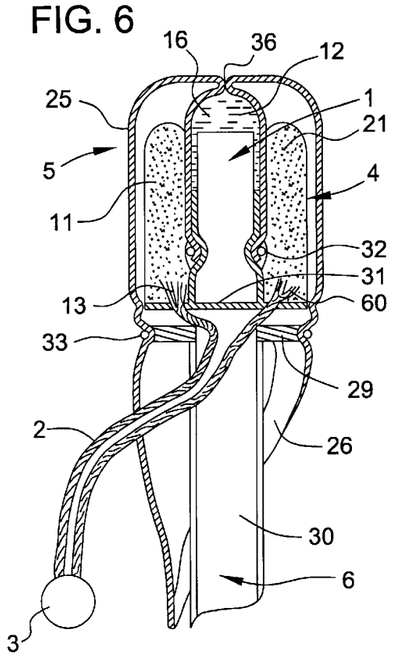
FIG. 6 represents an axial cross section of a device according to a second embodiment of the invention.
Figure 7:
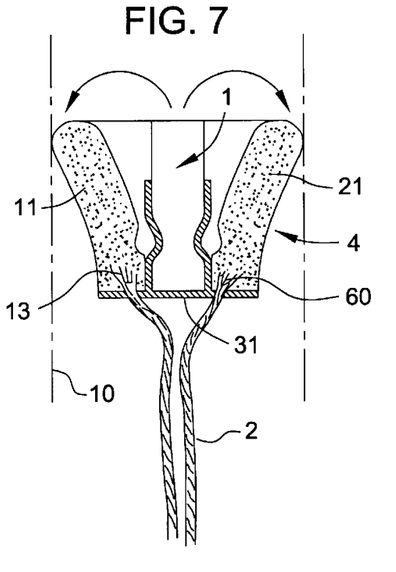
FIG. 7 represents an axial cross section of the peripheral and axial elements of the device represented in FIG. 6, once introduced and held in an intracorporeal cavity, after the temporary means of protection of the peripheral element has been removed.

The device represented in FIGS. 6 and 7 differs from the device represented in FIGS. 1 to 5 in terms of the following characteristics:

- in contrast to the device described above, the source 12 of the active liquid is contained in the central element 1, and the recovery means 13 60 in another embodiment for the active liquid, which has circulated in the intracorporeal cavity 10, is contained in the peripheral element 4; correspondingly, the transport element 2 is in continuity at one end with the peripheral element 4;
- the central element 1 comprises or consists of a cavity 16 containing the active liquid, this cavity being partitioned or defined by the sheath 25, closed back on itself via a seal or a weld 36.

Figure 8:
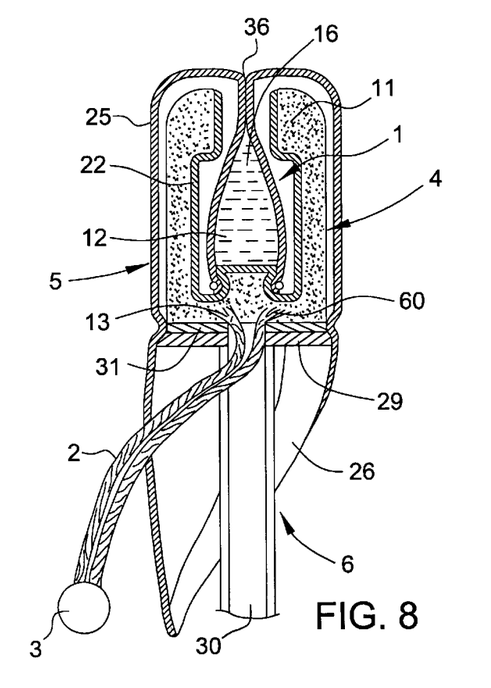
FIG. 8 represents an axial cross section of a device according to a third embodiment of the invention.
Figure 9:
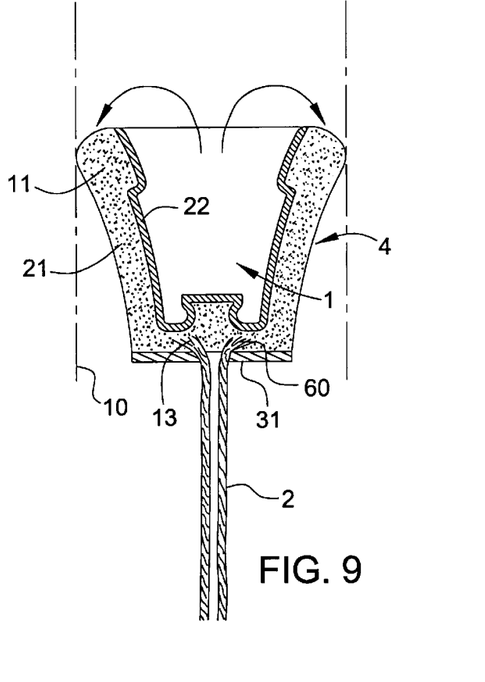
FIG. 9 represents an axial cross section of the peripheral and axial elements of the device represented in FIG. 8, once introduced and in position in an intracorporeal cavity.
Figure 10:
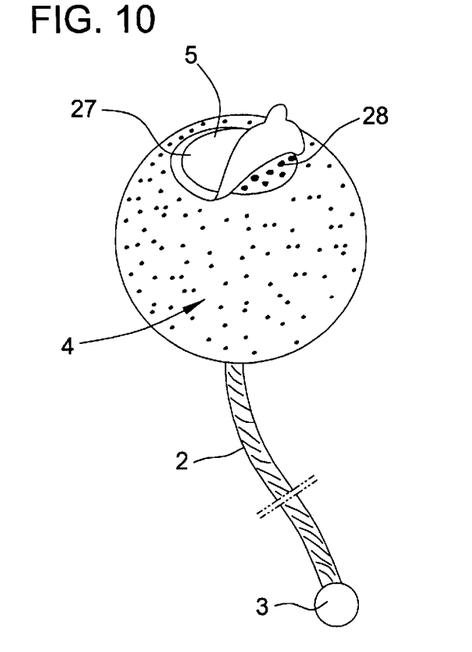
FIGS. 10 and 11 are perspective and sectional views, respectively, of a device according to a fourth embodiment of the invention.
Figure 11:
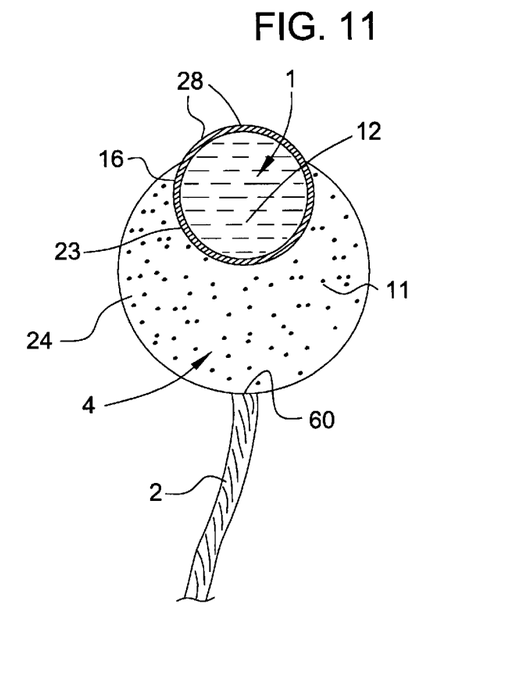

The device represented in FIGS. 8 and 9 differs from that represented in FIGS. 6 and 7 by the fact that a sealing partition 22 is formed between the central element 1 and the peripheral element 4.

The device represented with reference to FIGS. 10 to 13 differs from the device represented with reference to FIGS. 1 to 5 in terms of the following technical characteristics. The peripheral element 4 surrounds at least partially the central element 1, having the form of a cavity 16, itself consisting of an elastic and flexible material 23, for example rubber. The peripheral element 4 for its part consists of a material 24 capable of absorbing a liquid by expanding, for example a fiber-based material such as has been described above.

The temporary means of protection 5 consists of a capsule 27 which temporarily isolates holes 28, for passage of the active liquid, in relation to the peripheral element 4.

The application element 6 comprises a flange 37 which is fixed at the end of the axial rod 30 in such a way as to permit the accommodation of the transport element 2, extending between the peripheral element 4 held against said flange and the analysis element 3 held at the other end of the axial rod 30, consisting, as above, of a tube of open longitudinal section.

The capsule 27 is easily detachable in order to free the holes 28 at the moment of use, that is to say once the device has been put in place in the intra-corporeal cavity. From this moment, any pressure exerted on the cavity 16 permits its emptying, so that the active liquid impregnates the peripheral element 4 which, by soaking up said liquid, in turn compresses the cavity 16 in order finally to discharge the contents thereof.

Figure 12:
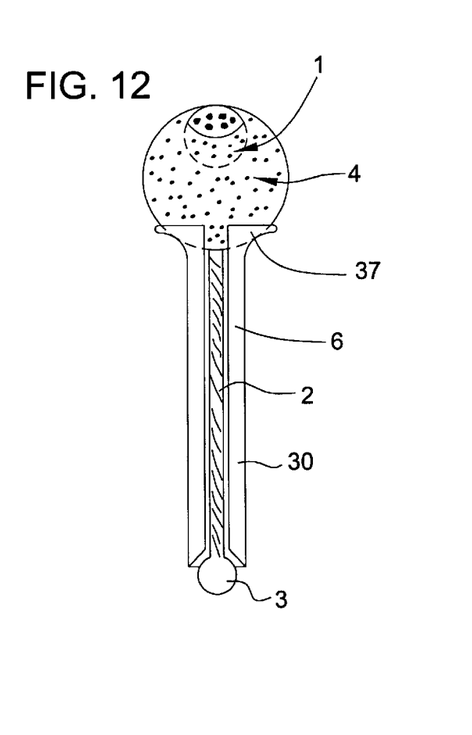
FIGS. 12 and 13 represent the device shown in FIGS. 10 and 11, connected to an application element and disconnected from the latter, respectively, in order to permit its detachment.
Figure 13:
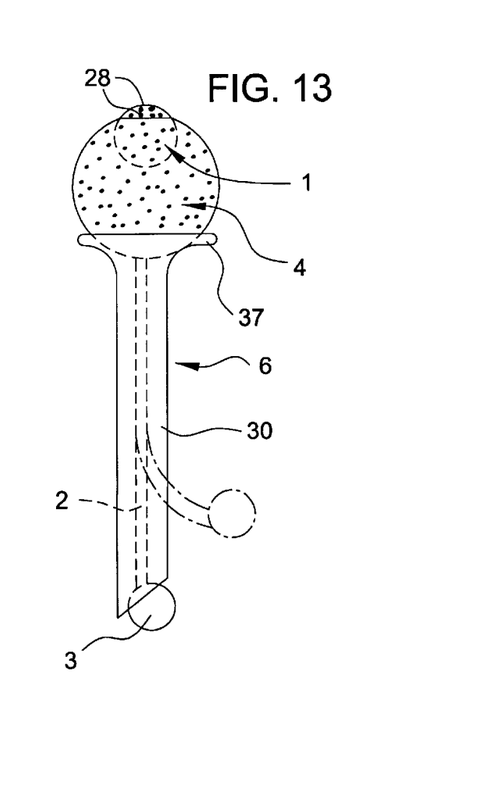

When the cavity 16 has been partially emptied, the analysis element 3 is pushed in front of the tube 30 in order to disengage the transport element 2 and to permit detachment and withdrawal of the application element 6 from the intracorporeal cavity. It then suffices, as in the case of the above devices, to pull on the transport element 2 in order to withdraw the assembly consisting of the central element 1 or cavity 16 and the peripheral element 4 of sphere shape.

In accordance with FIGS. 14 to 18, different devices according to the invention for the treatment of pathological lesions of the vaginal cavity are now described. For this purpose, the active liquid is a therapeutic liquid which can contain antibiotic or antiseptic products, hormone derivatives, corticoids, various emollients, local nutrients, etc.

Figure 14:
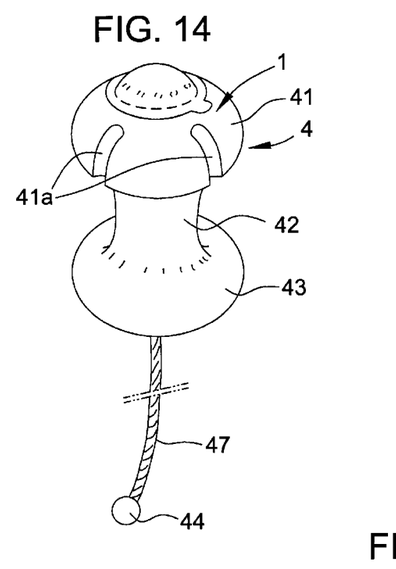
FIG. 14 is a perspective representation of a device according to a fifth embodiment of the invention, more particularly intended and adapted for the treatment of pathological lesions of the vaginal cavity.
Figure 15:
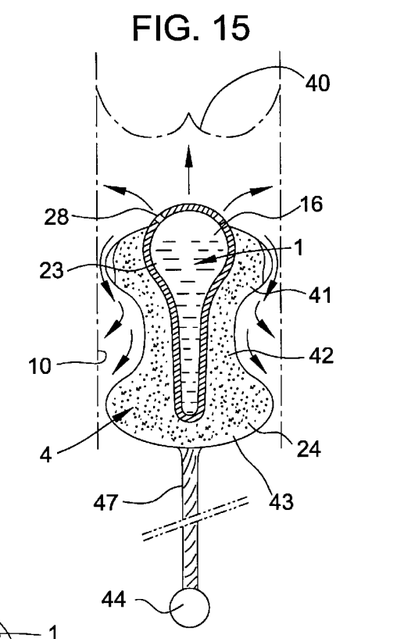
FIG. 15 represents the device shown in FIG. 14, in a diagrammatic cross section, and in position in the vaginal cavity.

In accordance with FIGS. 14 and 15, and in contrast to the embodiments represented and described above with reference to FIGS. 10 to 13, the peripheral element 4 comprises two bulged portions 41 and 43, on either side of a central core 42, of narrowed cross section, and thus generally has the shape of a "bobbin of thread". The cavity 16 containing the active liquid is arranged principally in the upper bulged portion 41, but also, in part, in the inside and at the center of the central core 42.

The bulged portion 41 in which the cavity 16 is arranged has various channels 41a for flow of the active liquid toward the central core, in contact with the vaginal wall, when the device is in place in the vaginal cavity 10 and abutting against the cervix 40. And this active liquid, if appropriate mixed with the vaginal flow, is finally recovered in the other bulged portion 43 of the peripheral element 4.

The device comprises a line 47 for removal from the vaginal cavity 10, said line being integral at one end of the peripheral element 4, and more precisely the other bulged portion 43, and comprising at the other end a gripping means 44.

The device described above proves to be well suited for preferential contact with the cervix, as is represented in FIG. 15.

The central core 42, which may or may not be of narrowed cross section, makes it possible, by virtue of the channels 41a, for the active liquid to reach the vaginal walls. This liquid is finally absorbed in the other bulged portion 43 of the peripheral element 4, if appropriate with all fluid oozing into the vaginal cavity, originating for example from a pathological flow, or a biological reaction triggered by the active medicinal liquid. Moreover, the other bulged portion can be impregnated with any suitable color reagent, making it possible for example to detect the toxins of the "microbes" destroyed by the active liquid. It is more precisely said other bulged portion 43 which makes it possible to avoid any substantial flow inside the vaginal cavity during the treatment of the latter with a device according to the invention.

Figure 16:
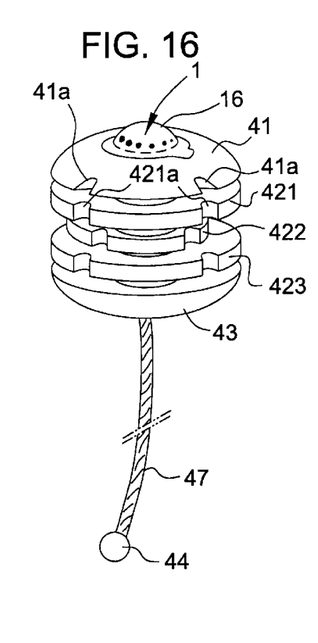
FIG. 16 represents a device according to a sixth embodiment of the invention, again intended and adapted for the treatment of the vaginal cavity.

The device represented in FIG. 16 differs from that represented in FIGS. 14 and 15 by the fact that:

the central core 42 has approximately the same cross section as the bulged portions 41 and 43 and includes a plurality of slices 421 to 423 which are separated and braced with respect to one another;

the slices 421 to 423 have notches, for example 421a, in line with one another and with a rib 41a for flow of the active liquid.

Figure 17:
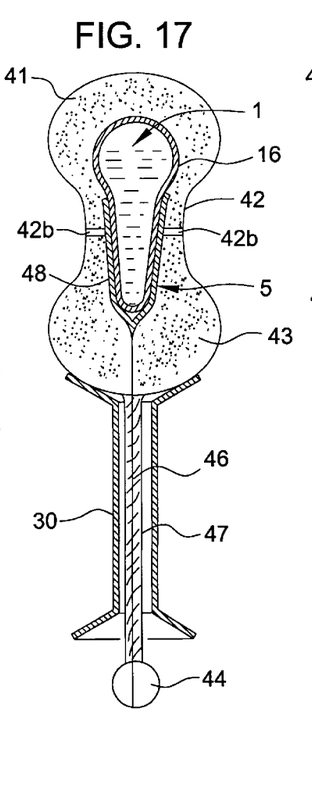
FIG. 17 represents a seventh embodiment of the invention, and more particularly a device for treatment of the vaginal cavity.

The device represented in FIG. 17 differs from that represented with reference to FIGS. 14 and 15 by the fact that, on the one hand, the central core 42 of the peripheral element 4 comprises orifices 42b for passage of the active liquid toward the outside and the vaginal wall, and, on the other hand, the temporary means of protection 5 comprises a removable sealing means 48 between, on the one hand, the inside of the cavity 16, and, on the other hand, the above-mentioned orifices 42b. This removable means is preferably an insulating sheath 48 which can be withdrawn separately by pulling on a string 46, from outside the vaginal cavity.

Figure 18:
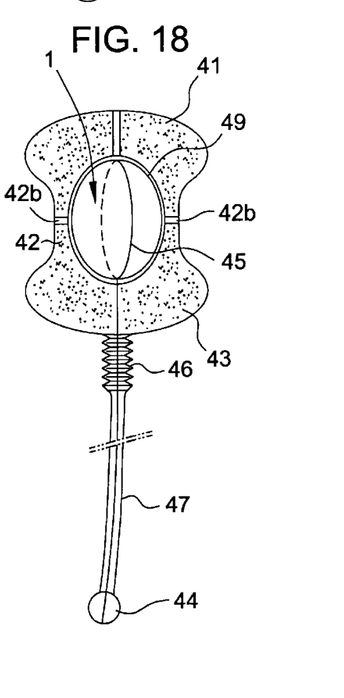
FIG. 18 represents in a diagrammatic manner an eighth embodiment of the invention, also consisting of a device for treatment of the vaginal cavity.

The device represented in FIG. 18 differs from that represented in FIG. 17 by the fact that the removable sealing means between the inside of the cavity 16 and the orifices 42b for passage of the active liquid comprises an envelope 49 delimiting the cavity 16, and means 45 designed to burst the envelope 49 and to be activated 46 in particular by pulling on the removal line 47.

Figure 19:
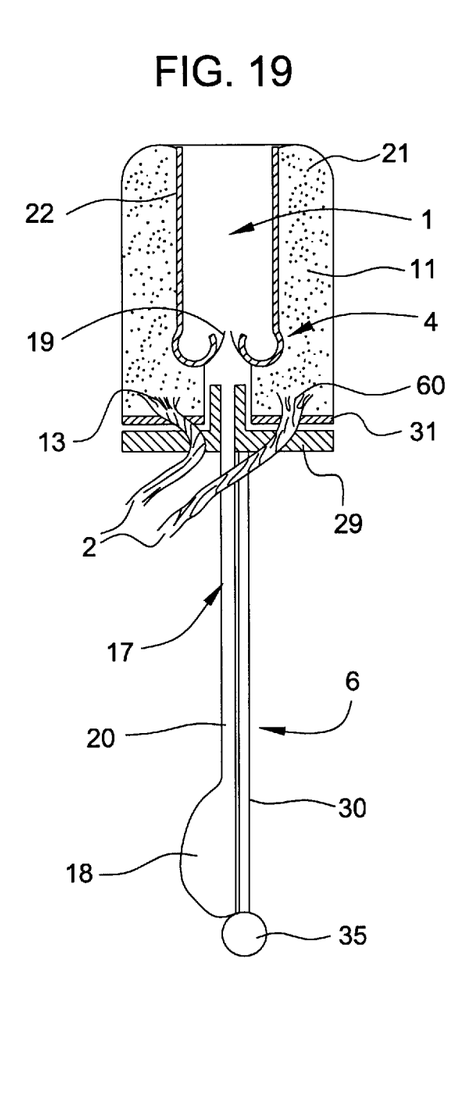
FIG. 19 represents a device according to a ninth embodiment of the invention, in axial section, and without its temporary means of protection of the spherical element.

The device represented in FIG. 19 differs from that represented in FIGS. 1 to 5 by the fact that the central element 1 comprises a means 17 for controlled introduction of the active liquid from the outside of the device. This means 17 has a flexible and depressible reservoir 18 arranged toward the end 35 of the axial rod 30, a flexible valve 19 arranged at the inlet of the central element 1 in the form of a cavity delimited by the sealing partition 22, and a conduit arranged between the reservoir 18 and the valve 19. The valve 19 is designed in such a way as to open in the direction of introduction of the active liquid and to close in the other direction.

I claim:

1. A disposable device for transfer of an active liquid into an intracorporeal cavity comprising:

a central element comprising an interior and an exterior surface, wherein the central element is able to contact the inside of said intracorporeal cavity;

an absorbent peripheral element arranged around the central element, wherein the peripheral element absorbs liquid and bears sealingly against mucous membranes of said intracorporeal cavity;

a temporary protective covering, sealed with respect to the liquids, that prevents fluid communication between the peripheral element and the interior surface of the central element, wherein the peripheral element and the central element are arranged to communicate with one another in said intracorporeal cavity, once the temporary protective covering has been withdrawn;

a source of the active liquid contained in the central element or the peripheral element;

a means for recovering the active liquid, which has circulated in the intracorporeal cavity, said means being contained in the peripheral element or the central element, respectively;

a transport element for transporting the active liquid that has circulated in the intracorporeal cavity, said transport element having an elongate shape and continuing at one end with the central element or the peripheral element; and an outer element for extemporaneous analysis of a constituent of a body fluid present in the intracorporeal cavity, mixed with the active liquid, wherein the outer element is arranged at a free end of the transport element.

2. The device as claimed in claim 1, wherein the source of the active liquid is contained in the peripheral element, and the recovery means for the active liquid which has circulated in the intracorporeal cavity is contained in the central element.

3. The device as claimed in claim 1, wherein the source of the active liquid is contained in the central element, and the recovery means for the active liquid which has circulated in the intracorporeal cavity is contained in the peripheral element.

4. The device as claimed in claim 1, wherein the central element comprises a core which is provided with filiform means, in particular capillary filaments, for contact with the mucous membrane of the intracorporeal cavity, said filiform means being held in shape by the temporary protective covering.

5. The device as claimed in claim 1 wherein the central element comprises a cavity containing the active liquid.

6. The device as claimed in claim 1 wherein the central element comprises a means for controlled introduction of the active liquid, from outside said device, in particular a flexible and depressible reservoir which is provided with a flexible valve cooperating with a conduit arranged along the axis of said device.

7. The device as claimed in claim 4, wherein the peripheral element comprises a sleeve of a material which is capable of absorbing a liquid by expanding, said sleeve surrounding the core provided with filiform elements.

8. The device as claimed in claim 5, wherein a sealing partition is formed between the central element and the peripheral element.

9. The device as claimed in claim 5, wherein the peripheral element surrounds at least partially the cavity, which itself consists of an elastic and flexible material, and said peripheral element consists of a material which is capable of absorbing a liquid by expanding.

10. The device as claimed in claim 1, wherein the temporary protection covering comprises a sheath enclosing at least partially, in a sealing manner, the peripheral element, all around the central element, and includes an attachment for pulling and exposing said peripheral element in the intracorporeal cavity.

11. The device as claimed in claim 10 wherein the sheath also partitions the cavity of active liquid.

12. The device as claimed in claim 9, wherein the temporary protective covering comprises a capsule which temporarily isolates holes, for passage of the active liquid, from the peripheral element.

13. The device as claimed in claim 1, which comprises an application element, mounted on the central element and/or the peripheral element, in such a way that it is integral in the direction of introduction into said cavity and in such a way that it is detachable in the opposite direction.

14. The device as claimed in claim 13, wherein the application element comprises a bearing element, which is fixed to an end of an axial rod.

15. The device as claimed in claim 14, wherein the central element is mounted sealingly at one end on a disk, in a manner aligned with the axial rod.

16. The device as claimed in claim 14 wherein the axial rod is adapted for passage of the transport element.

17. The device as claimed in claim 1, wherein the active liquid is selected from the group consisting of a wetting, solubilizing or fluidizing liquid agent, a therapeutic, prophylactic or diagnostic agent, a cosmetic agent or personal hygiene agent, and an antiseptic, bactericidal, fungicidal or spermicidal agent.

18. The device as claimed in claim 10, wherein said attachment is a loop.

19. The device as claimed in claim 14, wherein said bearing element is a disk or a flange.

20. The device as claimed in claim 14, wherein said axial rod is a tube.

21. The device as claimed in claim 1, wherein said transport element is a small cord.

22. The device as claimed in claim 1, wherein said peripheral element is concentric to said central element.

* * * * *